United States Patent [19]

Rydefalk et al.

[11] Patent Number: 4,689,988
[45] Date of Patent: Sep. 1, 1987

[54] DEVICE FOR SEPARATELY MEASURING PARTICLES IN A SUSPENSION

[75] Inventors: Staffan Rydefalk, Vallentuna; Jens Einarsson, Stockholm, both of Sweden

[73] Assignee: Svenska Traforskningsinstitutet, Stockholm, Sweden

[21] Appl. No.: 795,347

[22] PCT Filed: Feb. 13, 1985

[86] PCT No: PCT/SE85/00073
§ 371 Date: Oct. 15, 1985
§ 102 Date: Oct. 15, 1985

[87] PCT Pub No: WO85/03774
PCT Pub Date: Aug. 29, 1985

[30] Foreign Application Priority Data

Feb. 14, 1984 [SE] Sweden ................. 8400784

[51] Int. Cl.$^4$ ........................... G01N 15/07
[52] U.S. Cl. ........................ 73/61 R; 73/53
[58] Field of Search ............ 73/61 R, 61.1 R, 53

[56] References Cited

U.S. PATENT DOCUMENTS 3,728,893  4/1973  Janssen ................. 73/32 A
4,112,741  9/1978  Kerfoot et al. ........... 73/61.1 R
4,266,188  5/1981  Thompson ............... 73/61.1 R
4,441,960  4/1984  Karnis et al. ............ 73/61 R Primary Examiner—Stewart J. Levy
Assistant Examiner—Hezron E. Williams
Attorney, Agent, or Firm—Cushman, Darby & Cushman

[57] ABSTRACT

A measuring device by which it is possible to measure individually the content of each type of substance in a suspension with at least two types of suspended substances provided the density of the substance in each type is approximately equal and the densities of the substances included in the individual types are known. The measuring device comprises a density meter (10) known per se arranged to measure the density of the suspension and the density of the liquid in which the substances are suspended in order to determine the difference in density. Moreover, the measuring device comprises an apparatus (12) known per se and intended for measurement of particle concentration, which is arranged to measure the ratio of the volume of the suspended substances to the volume of the liquid. Finally, the measuring device also comprises a calculating unit (26) electrically connected to the density meter and the apparatus for measurement of particle concentration. The calculating unit is arranged to combine signals received from the density meter (10) and said apparatus (12) in order to calculate the concentrations of each of the substance types on the basis thereof.

9 Claims, 5 Drawing Figures

DEVICE FOR SEPARATELY MEASURING PARTICLES IN A SUSPENSION

BACKGROUND OF THE INVENTION

This invention relates to a device for measuring individually the content of each type of substance in a suspension with at least two types of suspended substances provided the density of the substance in each type is approximately equal and the densities of the substances included in the individual types are known.

In preparation of paper, especially fine paper, a so-called stock is used, which consists of a mixture of fiber material and filler, usually kaolin, in a suspension. The stock is applied to the endless wire of a paper making machine, part of the particles of the stock remaining on the wire and forming a sheet while the remaining part of the particles passes through the wire together with the major portion of the liquid and forms the so-called white water. The term retention is used as a measure of the efficiency of the paper making machine. This term is the quotient between the particle material forming the sheet and the material supplied to the wire. Addition of chemicals will enable a control of the retention, which will make it possible, among other things, to give the sheet a high content of filler. In order to enable control of the retention measuring equipment is needed giving a measure of the retention, especially for the two particle types individually, as it may be difficult to obtain a sufficient retention of filler. In the control the so-called first pass retention is interesting, which is defined $$1 - S_{BV}/S_{IL}$$

where
 $S_{IL}$ = the concentration of studied particle type of the suspension applied to the paper making machine.
 $S_{BV}$ = the corresponding concentration of the particles of the white water.

Now the acute need is to measure the concentration of filler of stock and white water independently of the presence of fiber material. A procedure often used with retention control comprises measurement of turbidity and density each separately. In measurement of the turbidity which is most sensitive to clay a device is used in which the damping of light passing through a particle suspension is determined. The essential disadvantage of this procedure is the dependence of a signal sensitivity on the particle size. Difficulties will arise in establishing whether the particle concentration or the particle size or both have changed when the resulting measuring signal is changed. Certainly the density measurement is sensitive to the change in concentration of the investigated suspension but measurement of clay is disturbed by the presence of fibers. For physical reasons there is no great changes of success when combining turbidity and density measurement.

SUMMARY OF THE INVENTION

It has now surprisingly been found according to the invention that two quite different properties of the suspension can be determined by a suitable arrangement of two measuring instruments known per se measuring two different properties of a suspension. Thus, a measuring device of the kind mentioned in the introductory section above comprises according to the invention a density meter known per se arranged to measure the density of the suspension and the density of the liquid in which the substances are suspended, for determination of the density differences; an apparatus known per se and intended for measurement of the particle concentration, which is arranged to measure the ratio of the volume of the suspension substances to the volume of the liquid; and a calculating unit electrically connected to the density meter and the apparatus, which unit is arranged to combine signals received from the density meter and the apparatus in order to calculate the concentrations of each the substance types on the basis thereof. As the density of cellulose and clay is higher than the density of water the density of a suspension of cellulose and clay particle will be dependent on concentration. The essential advantage of density measurement is its independence of particle size. The essential disadvantage is that the measuring signal must be adjusted with respect to the fiber concentration sensed by the density meter with another sensitivity constant. This adjustment is carried out using said particle concentration meter which is capable of suppressing the contributions from small particles such as clay but otherwise is independent of particle size. This compensation functions excellently as the volume content of the paper pulp of fine material is insignificant. One restriction is that the suspensions must not contain too much dissolved material if water is used as reference and not filtrate from the suspension.

According to the invention the calculating unit indicated above must be so embodied that the following calculations are possible $$S_F = k_a U_1 + k_b U_2$$

$$S_M = k_c U_1 + k_d U_2$$

where p1 $S_F$ is the content of suspended substances of the first substance type,
 $S_M$ is the content of the suspended substance of the second substance type,
 $U_1$ is the signal received from the density meter by the calculating unit,
 $U_2$ is the signal received from the apparatus for measurement of particle concentration by the calculating unit, and
 $k_a$, $k_b$, $k_c$ and $k_d$ are constants of proportionality.

The invention will now be described more in detail below in the form of preferred illustrative examples with reference to the appended drawing.

DESCRIPTION OF ILLUSTRATIVE EMBODIMENTS

Figure 1:
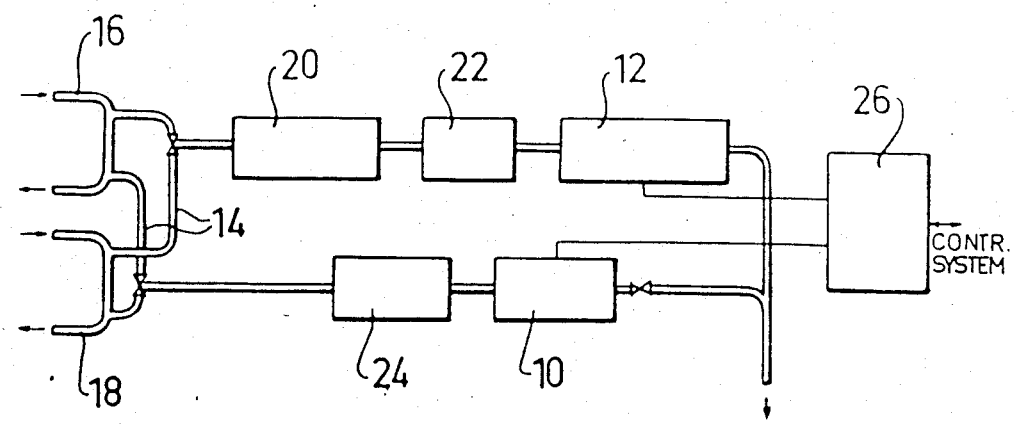
FIG. 1 shows schematically connection and disposition of the measuring device disclosed according to the invention, which is intended for separate concentration mesurement of substances in a suspension.
Figure 2:
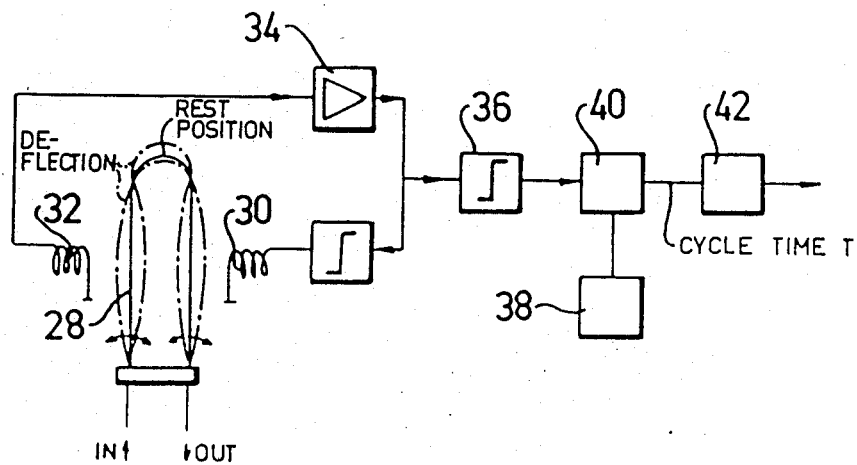
FIG. 2 shows the fundamental construction of the density meter disclosed in FIG. 1.

According to the arrangement in FIG. 1 a density meter 10 known per se and an apparatus 12 known per se for measurement of particle concentration are connected in the system of conduits 14 associated with the head box 16 and pulp water 18 of a paper making machine. There is a dispersing unit 20 and a diluting unit 22 between the apparatus 12 for measurement of particle concentration and the head box 16. There is a pressurization unit 24 between the density meter 10 and the conduit 18 for pulp water. Both the apparatus 12 for measurement of fiber concentration and the density meter 10 are connected to a calculating unit 26 which, thus, combines signals received from the meter and the apparatus in order to calculate the concentrations of each of the substance types on the basis of the densities of the two types of substances.

The principle of the density meter 10 is based on the condition that the resonance frequency of a mechanical oscillator is dependent of the mass thereof. In this case the mechanical oscillator consists of a U-shaped pipe 28 e.g. made of steel or glass containing the test suspension to be calculated. Thus, the mass of the oscillator constitutes the sum of the mass of the pipe 28 and the mass of the sample. An activation coil coacts with said U-shaped pipe 28. A pick-up coil 32 is connected to a Schmitt-trigger 30 via an amplifier 34. This delivers a pulse train to a counter 40 controlled by a clock 38 and the period time (T) of the oscillator is transmitted to a data processing unit 42 for calculation of the density of the suspension.

A suspension of the intended type consists of three components, viz. liquid, suspended material of type M and suspended material of type F.

Densities of the individual components are
$\rho_L$ density of the liquid
$\rho_M$ density of material M
$\rho_F$ density of material F The density is for example measured by determination of the weight $m_0$ of a definite volume $V_0$:

$$\rho = m_0/V_0$$

The total volume $V_0$ consists on one hand of the volume of the liquid and, on the other hand, the volumes of the suspended particles;

$$V_0 = V_1 + V_M + V_F$$

where
$V_L$ is the volume of the liquid
$V_M$ is the total volume of the particles of type M in $V_0$
$V_F$ is the total volume of the particles of type F in $V_0$.

The total mass $m_0$ is composed of the sum of the masses of the included components;

$$m_0 = m_L + m_M + m_F$$

where
$m_L$ is the mass of the liquid
$m_M$ is the total mass of the suspended particles of type m
$m_F$ is the corresponding of type F.

The density of the suspension can thus be expressed;

$$\rho = \frac{m_0}{V_0} = \frac{1}{V_0}(m_L + m_M + m_F)$$

Now the following applies:

$$m_L = \rho_L V_L$$

$$m_M = \rho_M V_M$$

$$m_F = \rho_F V_F$$

Thus the following is obtained;

$$\rho = \frac{1}{V_0}(\rho_L V_L + \rho_M V_M + \rho_F V_F)$$

What is interesting is now the change of the density arising when particles are suspended in a liquid:

$$\Delta\rho = \rho - \rho_L = \frac{1}{V_0}(V_L \rho_L + V_M \rho_M + V_F \rho_F) - \rho_L.$$

Moreover, one is most interested of expressing the presence of the suspended materials in their relative concentrations (weight of suspended material divided by the volume of the suspension).

$$S_M = \frac{\rho_M V_M}{V_0}$$

$$S_F = \frac{\rho_F V_F}{V_0}$$

This gives:

$$\Delta\rho = S_M + S_F + \frac{V_L \rho_L}{V_0} - \rho_L$$

but $$V_L = V_0 - V_M - V_F$$

i.e.

$$\Delta\rho = S_M + S_F + \frac{V_0 - V_M - V_F - V_0}{V_0}\rho_L =$$

$$= S_M - \frac{V_M}{V_0}\rho_1 + S_F - \frac{V_F}{V_0}\rho_L$$

The volume quotients can however be expressed by means of the concentrations:

$$\frac{V_M}{V_0} = \frac{1}{\rho_M} S_M$$

$$\frac{V_F}{V_0} = \frac{1}{\rho_F} S_F$$

The following is obtained inserted in the equation of $\Delta\rho$ $$\Delta\rho = S_M - S_M \frac{\rho_L}{\rho_M} + S_F - S_F \frac{\rho_1}{\rho_1} =$$

-continued $$\left(1 - \frac{\rho_L}{\rho_M}\right) S_M + \left(1 - \frac{\rho_L}{\rho_F}\right) S_F$$

Let material M be cellulose, material F be kaolin and the liquid be water and you will obtain:

$$\rho_L = 1.0$$

$$\rho_M = 1.5$$

$$\rho_F = 2.6$$

i.e.

$$\rho = 0.33 S_M + 0.62 S_F$$

A more general derivation of n particle types gives in brief $$\Delta \rho = \rho - \rho_L = \frac{1}{V_0}\left(V_L \rho_L + \sum_{i=1}^{n} V_i \rho_i\right) - \rho_L =$$

$$\frac{V_L \rho_L}{V_0} - \rho_L + \sum_{i=1}^{n} S_i =$$

$$\frac{V_0 - \sum_{i=1}^{n} V_i - V_0}{V_0} \rho_L + \Sigma S_i =$$

$$\sum_{i=1}^{n} S_i - \frac{V_i}{V_0} \rho_L = \sum_{i=1}^{n} S_i - S_i \frac{\rho_L}{\rho_i} =$$

$$\sum_{i=1}^{n} \left(1 - \frac{\rho_L}{\rho_i}\right) S_i$$

The optical measurement apparatus 12 for measuring the particle concentration (cf. also Swedish application No. 7513524-4) included in the new measuring device will measure the relative volume of a suspension consisting of particles. However, the following reservation applies;

(1) At a particle length shorter than the apparatus constant $x_b$ the sensitivity of the apparatus is reduced towards zero with decreasing particle size.

(2) In a comparison of measurements on different kinds of particles it may be found that the sensitivity of the apparatus will become somewhat different due to the fact that the different materials have different optical properties.

Figure 3:
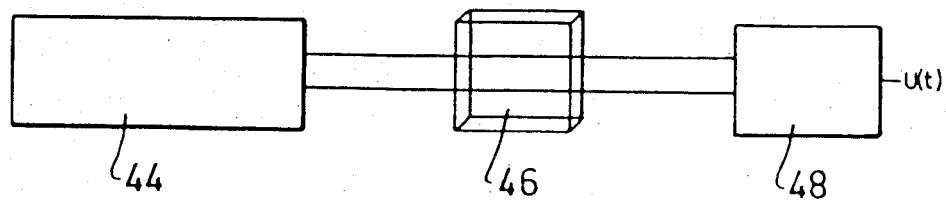
FIG. 3 shows the optical arrangement of the apparatus for measurement of fiber concentration included in the circuit according to FIG. 1.

In measurement of the particle concentration by the apparatus illustrated in FIG. 3 a light beam emitted from a light source 44 is passed through a cuvette 46 in which the relative suspension flows. The light detected in a detector 48 forms the rapidly varying output signal U(t). The signal U(t) has a maximized value corresponding to $U_0$. $U_0$ is then the signal passing out of the detector 48 in measurement on pure liquid without particles.

We start from the signal U(t) in the following calculation.

The mean value and standard deviation of the signal U(t) are first estimated. These values are both standardized with $U_0$, which will make the measurement independent of e.g. the absolute level of the light source.

The mean value is called $\tau$, as it will be the same as the mean transmission factor of the sample:

$$\tau = \frac{1}{U_0} <U>_t = \frac{1}{U_0}\left[\lim_{t \to \infty} \frac{1}{2T} \int_{-T}^{T} U(t) dt\right]$$

The standardized standard deviation is called $\sigma$ and is:

$$\sigma = \frac{1}{U_0} [<(U - <U>_t)^2>_t]^{\frac{1}{2}} =$$

$$\frac{1}{U_0}\left[\lim_{t \to \infty} \frac{1}{2T} \int_{-T}^{T} (U(t) - <U>_t)^2 dt\right]^{\frac{1}{2}}$$

The fluctuations of the light passing through will of cource be dependent on the particle content of the sample. A quantity, here called the fluctuancy $\phi$, is used as a measure thereof, the fluctuancy $\phi$ is calculated by the formula;

$$\phi = \nu \ln\left(\frac{\sigma^2}{\nu \tau^2} - 1\right)$$

$\nu$ is a linearizing constant which, if correctly selected, will make $\phi$ vary linearly to the particle concentration if other parameters such as particle size distribution etc. are kept at a constant.

If the suspensions of a certain type of particles could be prepared where all particles in the suspension had the same length it will be found that the concentration sensitivity of the fluctuancy has a characteristic appearance and it is drawn up against particle length.

Figure 5:
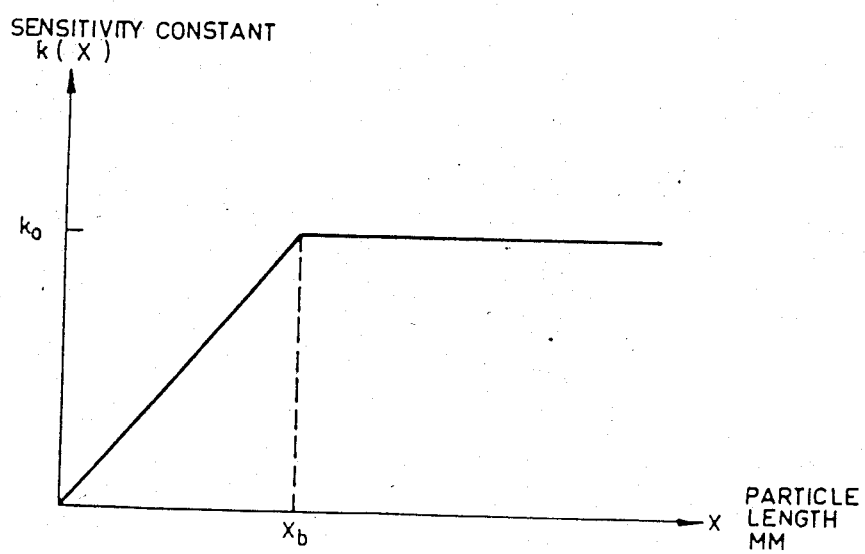
FIG. 5 shows the ratio of particle length to sensitivity of an apparatus according to FIG. 3.

Let x be the particle length and S(x) the concentration of particles of a certain length and k(x) the sensitivity constant of the apparatus at a certain particle length, i.e. $\phi = k(x)S(x)$ at a given x. The function k(x) will then have the form indicated in FIG. 5.

The break-point of the curve of the particle length $x_b$ can be varied by changing the diameter of the optical beam path. Thus the following is obtained:

$$k(x) = \begin{cases} x \cdot \frac{k_0}{x_b} & 0 < x \leq x_b \\ k_0 & x > x_b \end{cases}$$

In a sample composed of particles having a statistical density function of the concentration at a different particle length $$\frac{S(x)}{\int_0^{\infty} S(x) dx}$$

the fluctuancy will be $$\phi = \int_0^{\infty} k(x) S(x) dx$$

Thus, this applies to a sample of a certain particle type. In reality the apparatus 12 can of course not measure the weight of the particle, which is required at a determination of concentration. Instead that volume is to be measured which the particles take up relative to the total volume of the suspension passing the meter. Instead of $S(x)\rho V(x)/V_0$ should thus be used, i.e.

$$\phi = \int_0^\infty k(x)\rho \frac{V(x)}{V_0} dx = \{\text{let } K(x) = k(x)\rho\} = \int_0^\infty K(x) \frac{V(x)}{V_0} dx$$

If particles of different materials are suspended the function $K(x)$ will have the same form but different level, i.e. $K_i(x) = \text{const.} \ K_j(x)$ for materials "i" and "j". Thus, at n different particle types the following is obtained:

$$\phi = \sum_{i=1}^{n} \int_0^\infty K_i(x) \frac{V_i(x)}{V_0} dx$$

Special case 1. If all particles in the sample are longer than $x_b$, i.e. $V_i(x) \equiv 0$ if $x < x_b$ the following is obtained:

$$\phi = \sum_{i=1}^{k} K_{0i} \frac{V_i}{V_0} \text{ where } V_i = \int_0^\infty V_i(x) dx$$

Figure 4:
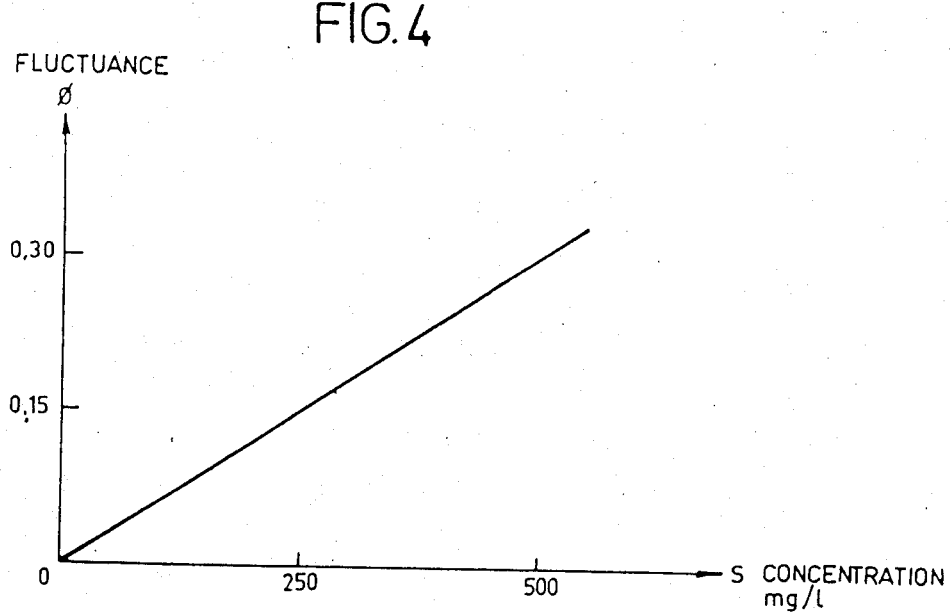
FIG. 4 shows the ratio of fluctuancy to particle concentration.

This means that the fluctuancy is a linear combination of the concentrations of the suspended particles (cf. FIG. 4);

$$\phi = \sum_{i=1}^{n} k_{0i} S_i$$

Special case 2. If the particles of a particle type are all essentially smaller than $x_b$ but the particles of the other particle types are bigger than $x_b$;

$$V_1(x) \equiv 0 \text{ for } \begin{cases} x > \epsilon \\ \epsilon < < x_b \end{cases}$$

$$V_i(x) \equiv 0 \text{ for } \begin{cases} x < x_b \\ i = [2 \ldots n] \end{cases}$$

This gives $$\phi \approx 0 + \sum_{i=2}^{n} K_{0i} \frac{V_i}{V_0} = \sum_{i=2}^{n} k_{0i} S_i$$

Special case 3. The particles are bigger than $x_b$ and the relative composition is known;

$$V_i = \alpha_i V \text{ where } \Sigma \alpha_i = 1$$

$$\phi = \sum_{i=1}^{n} K_{oi} \frac{\alpha_i V}{V_0} = \frac{V}{V_0} \sum_{i=1}^{n} K_{oi} \cdot \alpha_i = \text{known constant } \frac{V}{V_0}$$

Alternatively, the formulation can be made by means of the concentrations $$S_i = \beta_i S$$

where $\Sigma \beta_i = 1$ $$\phi = \Sigma k_{0i} \beta_i S = S \Sigma k_{0i} \beta_i = \text{known constant } S$$

SELECTIVE PARTICLE MEASUREMENT

Case 1. Known type of pulp and known type of filler are at hand

The system of equations $$\left. \begin{array}{l} \rho = a_{11} S_1 + a_{12} S_2 = U_1 \\ \phi = a_{21} S_1 + a_{22} S_2 = U_2 \end{array} \right\} <=> \overline{U} = \overline{AS}$$

is solved $$\overline{S} = A^{-1} \overline{U}$$

Case 2. Known type of filler and two types of pulp are at hand. It is assumed that the relative concentration ratio of the pulp types can be measured $$S_2 = \alpha S_2' S_3 = (1-\alpha) S_2 S_2' = S_2 + S_3$$

Two examples of a solution (1)

$$U_1 = a_{11} S_1 + a_{12} S_2 + a_{13} S_3$$

$$U_2 = a_{21} S_1 + a_{22} S_2 + a_{23} S_3$$

but $U_2$ can be written $$U_2 = 0 + \alpha a_{22} S_2' + (1-\alpha) a_{23} S_2'$$

and is solved in usual manner.

(2) Let instead $a_{12}$ and $a_{22}$ be functions of the pulp composition;

$$U_1 = a_{11} S_1 + a_{12}(\alpha) S_2$$

$$U_2 = a_{21} S_1 + a_{22}(\alpha) S_2$$

This is solved in usual manner.

Case 3. A known type of filler and two types of pulp are at hand. The pulp types are characterized in that they differ substantially as to mean fiber length, here called $<X>$ and $<X_3>$. One additional fluctuancy meter is introduced into the measuring system so that the following applies to the break-point $X_b$ thereof; $(X_b > <X_2>) \cap (X_b > <X_3>)$.

$$\rho = U_1 = a_{11} S_1 + a_{12} S_2 + a_{13} S_3$$

$$\phi_1 = U_2 = a_{21} S_1 + a_{22} S_2 + a_{23} S_3$$

$$\phi_2 = U_3 = a_{31} S_1 + a_{32} S_2 + a_{33} S_3$$

$$\begin{cases} a_{22} \approx a_{23} \\ a_{32} \neq a_{33} \end{cases}$$

These are solved in usual manner or referred back to case 2:2 by $$\alpha = f(\phi_2/\phi_1.)$$

We claim:

1. A device for measuring individually the content of each of at least two types of substances in a suspension wherein the density of each substance is approximately equal and known, said device comprising:

a density meter for measuring the density of the suspension and the density of the liquid in which the substances are suspended, in order to determine the difference in density; measuring means for measuring particle concentration and the ratio of the volume of the suspended substances and the liquid; and calculating means electrically connected to said density meter and measuring means to adjust the signal received from the density meter by use of the signal received from the measuring means according to the relationship:

$$S_F = k_a U_a + k_b U_2$$

$$S_M = k_c U_1 + k_d U_2$$

where $S_F$ is the content of suspended substance of the first type substance, $S_M$ is the content of suspended substances of the second type, $U_1$ is the signal received from the density meter by the calculating means, $U_2$ is the signal received from the measuring means by the calculating means for measurement of particle concentration and $k_a$, $k_b$, $k_c$ and $k_d$ are constants of proportionality.

2. The device of claim 1, wherein the constant $k_b$ is approximately equal to half the negative value of the constant $k_d$ and the constant $k_a$ is approximately as great as the negative value of the constant $k_c$, for measurement of wood pulp filler suspended in water.

3. The device of claim 1, wherein said measuring means for measurement of particle concentration is arranged to selectively measure a predetermined particle size, the constants $k_a$ and $k_c$ being selectable to obtain an improved measuring accuracy in the case when the particle types are also characterized by a great difference in distribution of particle size.

4. The device according to claim 1 wherein the density meter employs a means of vibration of a flowing suspension to achieve measurement.

5. The device according to claim 1 wherein the measurement means for measurement of particle concentration employs optical techniques on a flowing suspension to achieve measurement.

6. The device according to claim 2 wherein the density meter employs a means of vibration of a flowing suspension to achieve measurement.

7. The device according to claim 3 wherein the density meter employs a means of vibration of a flowing suspension to achieve measurement.

8. The device according to claim 2 wherein the measuring means for measurement of particle concentration employs optical techniques on a flowing suspension to achieve measurement.

9. The device according to claim 3 wherein the measuring means employs optical techniques on a flowing suspension to achieve measurement.

* * * * *